United States Patent [19]

Wienck

[11] Patent Number: 4,858,477
[45] Date of Patent: Aug. 22, 1989

[54] DRY MATERIALS SAMPLE COLLECTOR IMPROVEMENTS

[75] Inventor: Dennis A. Wienck, Duncan, Okla.

[73] Assignee: Halliburton Company, Duncan, Okla.

[21] Appl. No.: 211,315

[22] Filed: Jun. 24, 1988

[51] Int. Cl.$^4$ ............................................. G01N 1/20
[52] U.S. Cl. ............................. 73/863.54; 73/863.82; 73/863.86
[58] Field of Search ........... 73/863.54, 863.58, 863.52, 73/863.53, 863.82, 863.83, 863.84, 864.64, 863.86

[56] References Cited

U.S. PATENT DOCUMENTS

| | | |
|---|---|---|
| 3,005,347 | 10/1961 | Smithson . |
| 3,659,461 | 5/1972 | Thompson . |
| 3,690,179 | 9/1972 | Olson . |
| 4,055,088 | 10/1977 | Diss . |
| 4,076,420 | 2/1978 | De Maeyer et al. ............ 356/313 X |
| 4,082,004 | 4/1978 | Weber et al. . |
| 4,120,203 | 10/1978 | Clements et al. . |
| 4,170,900 | 10/1979 | Ozawa . |
| 4,269,064 | 5/1981 | Johnson et al. ................... 73/863.82 |
| 4,479,393 | 10/1984 | Shores ................................ 73/863.82 |
| 4,530,236 | 7/1985 | van den Berg .............. 73/864.45 X |
| 4,538,472 | 9/1985 | Skarpness ......................... 73/863.55 |
| 4,562,747 | 1/1986 | Jaeger ............................... 73/863.54 |
| 4,682,506 | 7/1987 | Wienck et al. ................... 73/863.54 |

FOREIGN PATENT DOCUMENTS 106765 4/1984 European Pat. Off. ......... 73/863.54

OTHER PUBLICATIONS

Gustafson, Inc., Automatic Sampling Systems Sales Brochure; 30 pages; published by Aug. 1988.
InterSystems Industrial Products, Inc. Sales Brochure; "Automatic Industrial System InterSystems Samplers"; 34 pages, pub. by Aug. 1988.
Quality Control Equipment Company Sales Brochure, "Samplers/Flowmeters"; 10 pages; Feb. 1985.

Primary Examiner—Tom Noland
Attorney, Agent, or Firm—Mark E. McBurney

[57] ABSTRACT

An improved dry material sample collector is provided which allows a cross-section of conveyed bulk material to be intermittently sampled. A collection head, mounted upon the piston of a pneumatic cylinder, is extended into a bulk material conveying line at specific intervals. The pneumatic cylinder piston is of a hollow construction and provides a path through which the sample material flows. A piston guide, or a stabilizing arm, maintains the collection head perpendicular to the flow of conveyed material so that a homogenous sample is retrieved. Additionally, a pneumatic control system provides power to the pneumatic cylinder and allows the time interval between sampling operations to be varied, thereby controlling the amount of sample material obtained.

22 Claims, 7 Drawing Sheets

DRY MATERIALS SAMPLE COLLECTOR IMPROVEMENTS

BACKGROUND OF THE INVENTION

In many industries there exists a need to obtain a sample of liquid, gaseous or dry material for quality control purposes, or the like. Often times the material is being transported via tubing, pipe, conduit or other enclosed conveying means. A problem arises in that the representative sample of material must be retrieved from the conveying pipe without impeding the flow of the bulk of the material.

In the oil and gas industry, casing is cemented into wells using different blends of cement for different applications. To achieve the proper blend, different ingredients such as cement, sodium chloride and silica are often conveyed under positive (pressures above atmospheric pressure) via pipes or tubes from a bulk storage tank to a blending unit. Therefore, it is highly desirable to have a device which can accurately and economically take a sample of material at the blending unit of the bulk plant so that the composition of cement actually used at the job site can be compared with the samples taken. Further, the blended cement mixture may not be totally homogeneous in nature, therefore it is also desirable to have a material sampling device which can take a crossection of the material to be sampled.

Several devices are currently known which can obtain material samples, for example, U.S. Pat. No. 4,082,004 to Weber et al shows a cross cut sampler which can take a cross sectional sample of material from a housing connected within a conveying tube. The material sample is then conveyed through a hose to a sample container. This devices uses an externally connected air cylinder to insert and retract the sample head into, and out of the housing. Further, a closure is used which physically abuts the front face of the sample head, while in the retracted position.

U.S. Pat. No. 4,120,203 to Clements et al shows a crosscut sampler for pneumatic conveying systems. A sample head is positioned alongside a conveying pipe and moved perpendicularly across the flow of the conveyed material by an external air cylinder.

Further, U.S. Pat. No. 3,659,461 to Thompson shows a plunger with an inclined baffle attached to the rod of a hydraulic cylinder. The plunger is insertable into a product supply line upon actuation of the hydraulic cylinder. Each of the aforementioned patents utilizes an air or hydraulic cylinder externally connected to a sampling head, which is movable through the conveyed material. The present invention utilizes a cylinder with a piston which is of a hollow construction, wherein the piston is used to convey the material sample from the sampling head to a sample storage area. Therefore, the present invention, by incorporating the cylinder into the sample conveying path, provides a more efficient, simple and compact sampling device than disclosed in any of the aforementioned prior art devices.

SUMMARY OF THE INVENTION

The present invention provides a material sampling apparatus which overcomes the shortcomings of the aforementioned prior art devices. The present invention allows a crossection of material to be sampled as it flows through a conveying tube in a pressurized (pressure above atmospheric pressure) system, and further is relatively inexpensive to construct and simple to operate.

Broadly, the material sampling apparatus includes a collection head which receives the material to be sampled as it flows through a conveying tube, pipe or conduit. A sample storing area is provided which allows the sampled material to be stored during the duration of the sampling process. The storing area includes a container which is removable from the material sampling apparatus, such that the material may be readily handled for testing, shipping, storage, or the like.

A sample conveying system is included which provides a path from the collection head to the sample storing area. The sample material is moved through the conveying system by the pressure exerted upon the sample by the bulk of the material being conveyed through the conveying tube. The sample conveying system includes a cylinder piston rod which is of a hollow configuration. The cylinder is utilized to move the collection head into and retract the collection head from the path of the bulk material being conveyed in order to obtain the sample. Further, a control system is provided which allows the frequency at which samples are taken to be regulated.

Therefore, in accordance with the previous summary, object, features and advantages of the present invention will become apparent to one skilled in the art from the subsequent description and the appended claims taken in conjunction with the accompanying drawings.

DETAILED DESCRIPTION OF THE PREFERRED EMBODIMENTS

Figure 1:
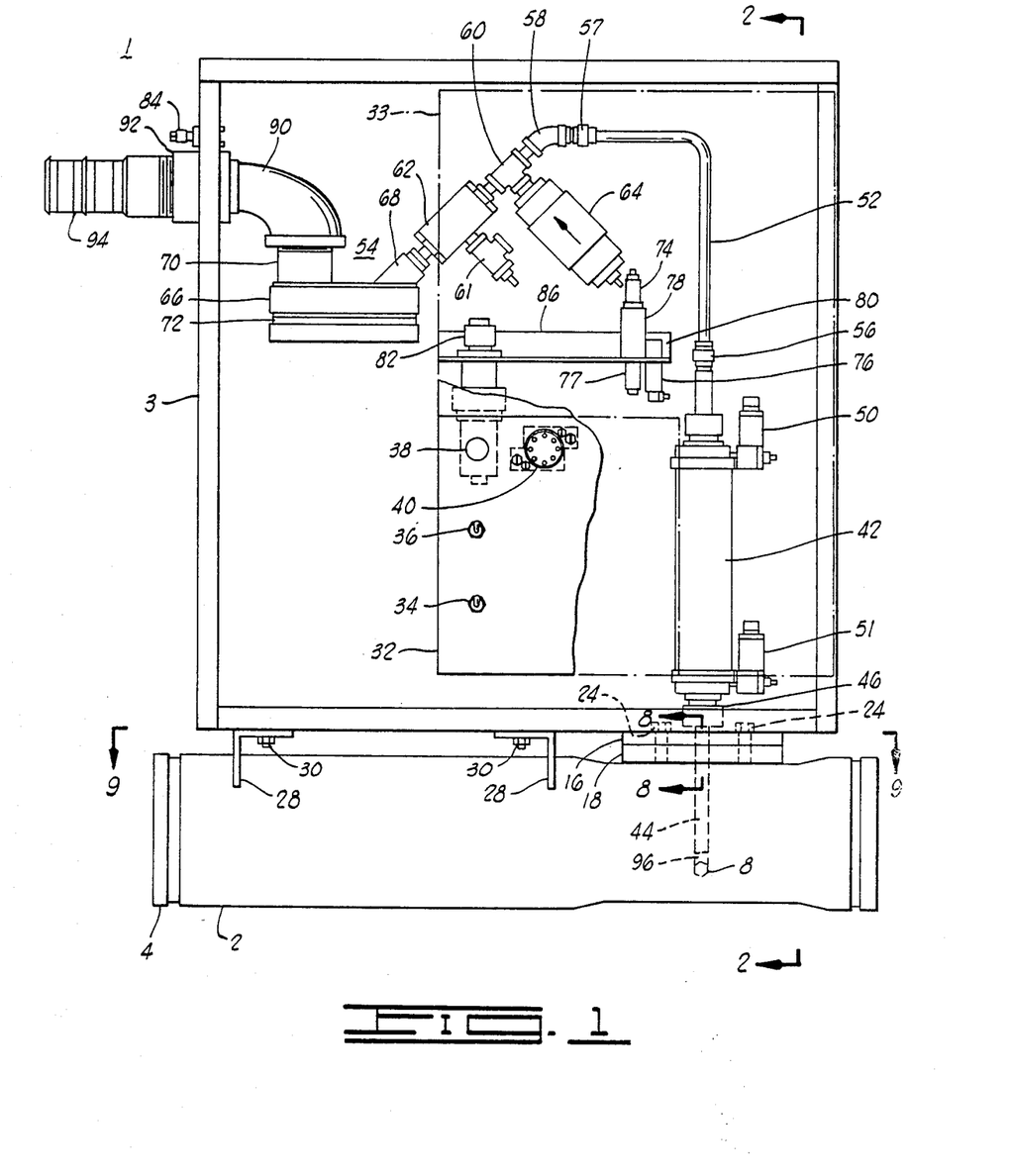
FIG. 1 is a front elevational view showing the components of a first preferred embodiment of the present invention.

Referring to FIG. 1, a first preferred embodiment of a material sampling device is shown and generally depicted by reference numeral 1. An enclosure 3 is included which is configured as a rectangular box, as is well known in the art and is constructed of sheet metal or the like, with cutouts and drilled holes therein, as required. Enclosure 3 contains the various components of sampling device 1, to be discussed in detail below.

A conveying portion 2 is connected in series with a bulk material conveying pipe (not shown) using a connecting portion 4 such as a clamp with victaulic ends, or the like. Conveying portion 2 tapers from a circular crossectional area at each end to a substantially square crossectional area 6 (FIG. 2) in the vicinity where a sample collection head 8 is insertable into the conveying portion 2. Sample collection head 8 enters conveying portion 2 via a rectangular cutout area 10 (FIG. 9) and a square cutout area (not shown) on the bottom of enclosure 3. A collection head housing, generally depicted by reference numeral 14 (FIG. 8) includes a plate 16 and a mounting rim 18 (see FIGS. 8 and 9). Mounting rim 18 encompasses rectangular cutout area 10 and includes a recessed area 20 (FIGS. 8 & 9) such that an O-ring 22 can be disposed therein. Mounting rim 18 is attached to conveying portion 2 by welding, or the like. Threaded connectors 24, such as a nut and bolt, or screws, are used to affix mounting rim 18 to plate 16, with O-ring 22, or similar devices, providing sealing engagement therebetween.

Sample collection head 8 is housed within a holding area 6 (FIG. 8) when in a retracted position. In this position, collection head 8 does not obstruct the flow of bulk material through conveying portion 2.

Brackets 28 with threaded connectors 30, or the like, provide support between enclosure 3 and conveying portion 2. Brackets 28 are welded or otherwise attached to conveying portion 2 and connectors 30 then affix brackets 28 to enclosure 3.

Also shown in FIG. 1 is a panel 32 for mounting the controls for the sampling device 1 thereon. An on-off switch valve 34, short-long cycle delay switch valve 36, long delay adjustment switch valve 38, and short delay adjustment switch modular valve 40 are included on panel 32. Additionally, a cover panel 33 is included which shields the moving parts of sampling device 1, such as cylinder 42 (described below) from an operator during the time when valves 34, 36, 38 and 40 are being set.

Figure 4:
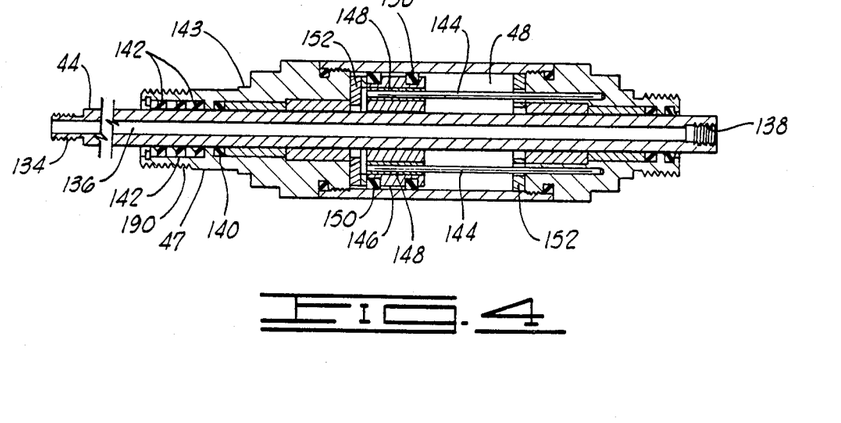
FIG. 4 is a crossectional schematic diagram of a cylinder and piston rod used for moving the collection head and transferring the sample material.

Pneumatic cylinder 42, including a hollow piston rod 44, is mounted within enclosure 3 and threadedly engages housing 14 via cylinder mounting 46 and threaded end portion 190 (FIG. 4), thereby rigidly affixing cylinder 42 to housing 14 and enclosure 3. A cylinder end portion 47 further provides a sealing engagement between the outside surface of piston rod 44, which is exposed to the bulk material being conveyed through conveying portion 2, and the inner chamber 48 (FIG. 4). Hollow piston 44 is extendable into conveying portion 2 through a square cutout portion on the bottom of enclosure 3, the interior cylindrical area 12 of cylinder mounting 46 and rectangular cutout portion 10 of housing 14 when cylinder 42 is mounted thereon. Hollow piston rod 44 is connected to collection head 8 by a connector 96 which is threadedly engaged with rod 44 and rigidly affixed to collection head 8 by welding, or the like. Collection head 8 is constructed of metal, or other similar material, as is known in the art.

Sensing valves 50 and 51, such as are commercially available as sensor fitting valves, manufactured by Legris, are connected on each end of cylinder 42 using a means which is known in the art. Sensing valves 50, 51 are air operated and control the movement of piston rod 44 based on the setting of valves 34, 36, 38 and 40, as discussed below.

A flexible sample tube 52 is connected to hollow piston rod 44 with a connector 56 which achieves an air tight sealing engagement. Next, flexible tube 52 connects (via a connector 57) to a 45° ell 58 which is in turn connected to a tee connector 60. The end of tee connector 60 opposite to ell connector 58 is connected to a pinch valve 62. Tee connector 60 is also connected to a check valve 64 which provides a one way path for air to flow towards collection head 8 and thus provides a means for purging the sample collection system.

Pinch valve 62 connects to sample storage portion 54 which includes a manifold portion 66 with a sample inlet 68 and an exhaust outlet 70. A container such as a bag, jar or the like (not shown) is connected to manifold portion 66 utilizing an O-ring type seal 72. A 90° ell 90, coupling 92 and nipple 94 are used to vent exhaust outlet 70 outside of enclosure 3. An air filter (not shown) can be connected to nipple 94, or connection to a plant filtration system can be made from nipple 94.

Material sampling device 1 also includes actuators 74 and 77, used in conjunction with a four-way valve 78 and an actuator 76, used in conjunction with a three-way valve 80. Additionally, an air filter/regulator 82 is included for regulating and filtering the air supply which is input from the plant air supply via an air input fitting 84. Actuators 74, 76, 77 and filter/regulator 82 are mounted within enclosure 3 using a bracket 86 which may be configured as a channel bracket, angle bracket, or the like. Threaded connectors 88 (FIG. 2) mount bracket 86 to enclosure 3.

Figure 2:
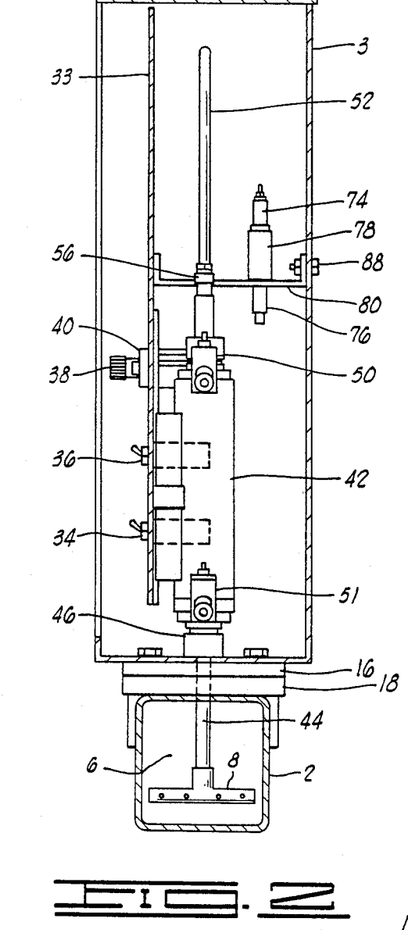
FIG. 2 is a side elevational view of the material sampling device of the present invention, taken along line 2—2 of FIG. 1.

FIG. 2 is a side elevational view of sampling device 1, taken along line 2—2 of FIG. 1. Reference numerals depicted in FIG. 2, and throughout the remainder of the drawings, refer to the same components of the present invention as described above with regard to FIG. 1. FIG. 2 contains essentially the same components previously described in regard to FIG. 1 and is included to provide the structural configuration of a first preferred embodiment of the present invention.

Figure 3:
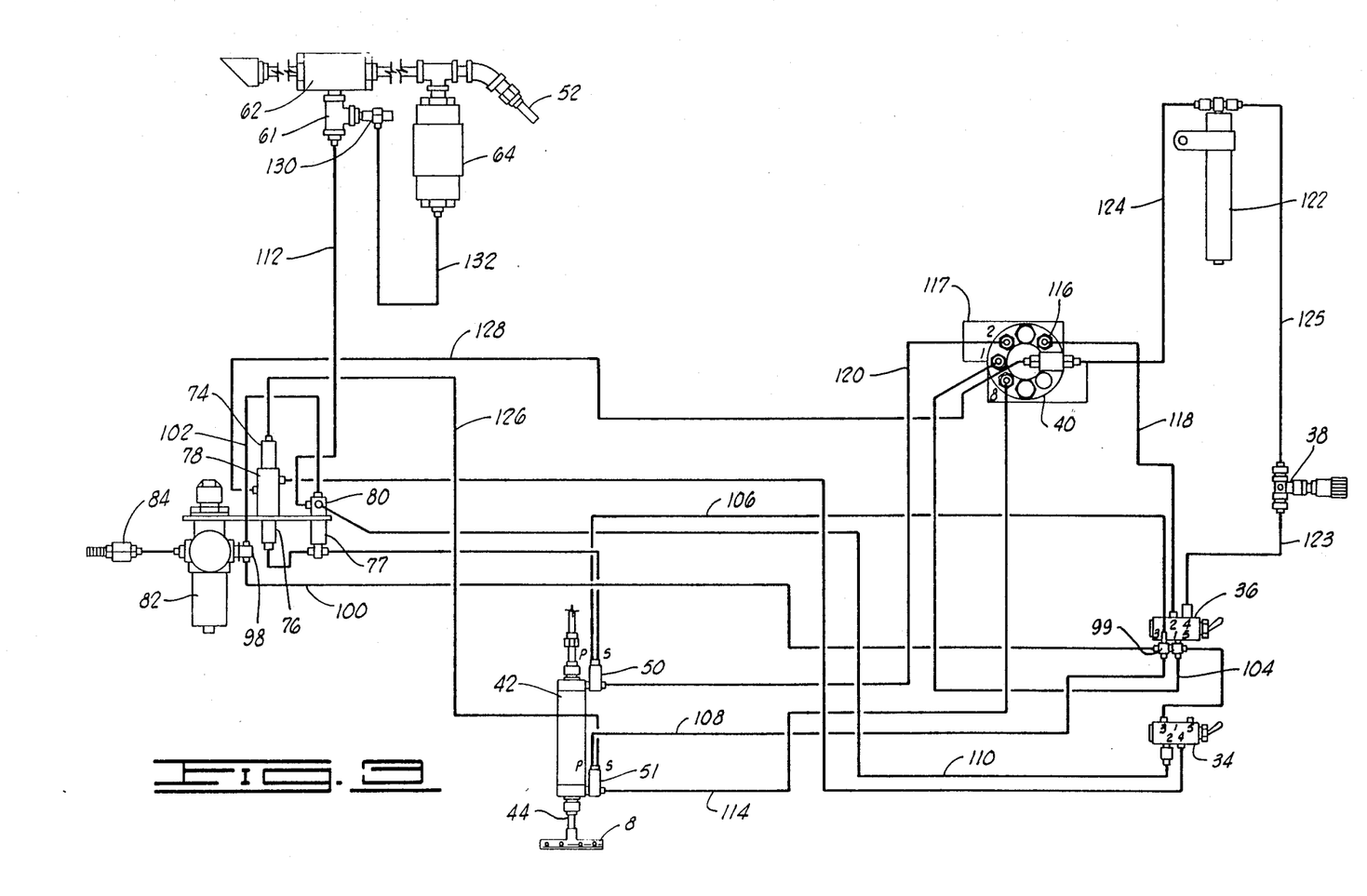
FIG. 3 is a schematic diagram of the pneumatic control circuit of the first preferred embodiment.

The operation of the pneumatic control system contained in enclosure 3 and mounted upon control panel 32 will now be described with reference to FIG. 3.

First, the control system will be described with collection head 8 in the retracted position and on/off valve 34 in the off position. Plant supply air is input through air fitting 84 and proceeds directly to filter/regulator 82, where the air supply is filtered and the pressure is regulated. The air supply is then split through a tee fitting 98 and is supplied to a distribution block 99 (affixed to short/long delay valve 36) through supply line 100, and to 3-way purge valve 80 through supply line 102.

Distribution block 99 then supplies pneumatic power to port 1 of short delay valve 40 (modular valve) via supply line 104, port 3 of on/off valve 34, and to each power (p) port of sensing valves 50 and 51, via lines 106 and 108, respectively. Sensing valve 50 supplies a pneumatic signal through line 111, to actuator 77.

During this phase of operation, air flows from port 3 to port 2 of on/off valve 34 and then from port 2, to 3-way valve 80 (purge valve) via supply line 110. A small amount of air will be vented from port 1 of on/off valve 34. Next, air will flow from purge valve 80 to pinch valve 62 (based on the signal received by actuator 77 from sensing valve 50) via supply line 112 and tee connector 61. The supplied air maintains pinch valve 62 in a closed position. Thus, with pinch valve 62 closed, no sample material will flow into the sample storage area 54. Modular valve 40 provides air to sensing valve 51 through line 114, maintaining hollow piston rod 44, and thus collection head 8 in the retracted position.

Still referring to FIG. 3, the operation of the sample device 1 of the present invention will be described wherein the collection head 8 is in a retracted position and the on/off valve 34 is in the "on" position.

Delay timing is initiated as soon as on/off valve 34 is switched on. The delay timing feature of the present invention allows for the frequency of the sampling cycle to be varied depending upon the batch size, and desired amount of sample to be retrieved.

Short/long delay valve 36, when in the "short" position, provides a short delay between samples by directing pneumatic power out of port 2 and into a needle valve 116, included within modular valve 40, via supply line 118. Needle valve 116 restricts the volume of air which is allowed to flow into a small volume chamber 117 which is also included within modular valve 40. A predetermined pressure must be built up in small volume chamber 117 before the pneumatic power is transferred on to valve 50 of cylinder 42. Thus, a time delay is achieved during the time period when the pressure within small volume chamber 117 is building to a predetermined level (such as 40 psi). This increase in pressure is controlled by needle valve 116 which regulates the volume of air allowed to flow into the chamber 117. Once the predetermined level is reached, pneumatic power is then transferred from port 2 of modular valve 40 to sensing valve 50, through line 120, to cylinder 42 thus extending hollow piston rod 44. Delays of up to approximately 30 seconds can be achieved using needle valve 116 and chamber 117 within modular valve 40.

A greater delay can be achieved by switching valve 36 to the "long" position. In this mode, pneumatic power is directed from port 4 to a chamber 122 through lines 123, 125 and long delay valve 38 (described below). Chamber 122 has a volume larger than chamber 117 contained in modular valve 40. While pneumatic pressure is increasing in chamber 122, air is freely directed to modular valve 40. This air bypasses needle valve 116 and is supplied directed to chamber 117 of modular valve 40. Thus, in the long delay mode, volume chambers 117 and 122 are effectively connected in a parallel arrangement such that their volumes are combined. Once a predetermined pressure within modular valve 40 is reached, pneumatic pressure is directed to valve 50 and cylinder 42 through line 120 as described above. It should be noted that chamber 122 does not restrict air flow until a predetermined pressure level is reached within modular valve 40. Additionally, long delay adjustment valve 38, such as a manually operated needle valve is provided which restricts the volume of air which flows into chamber 122, thus controlling the amount of time required before the predetermined pressure level within modular valve 40 is reached and air can be supplied to operate cylinder 42. By adjusting valve 38, a fine tuning function can be achieved, and several long delay settings are possible.

Once air is supplied to valve 50 from modular valve 40, piston rod 44 starts extending downward. Simultaneously, sensing valve 50 ceases to send a signal to actuator 77, and the air supply to pinch valve 62, via line 112, is stopped. Therefore, pinch valve 62 opens allowing sample material to flow from collection head 8, which has been inserted into conveying portion 2, to sample storage area 54.

When piston rod 44 reaches its fully extended position into conveying portion 2, sensing valve 51 sends a signal to actuator 74 through supply line 126, which causes 4-way valve 78 to shift and release air from chamber 117 of modular valve 40, via line 128, causing it also to shift. The shifting of modular valve 40 causes the air supply to be transferred (via port 8 and supply line 114) from sensing valve 50 to sensing valve 51 causing piston rod 44 to begin retracting from conveying portion 2. Pinch valve 62 remains open while rod 44 is being retracted and the flow of sample material continues during this period. After rod 44 becomes fully retracted, sensing valve 50 sends a signal through line 111 to actuators 76 and 77, and actuator 77 closes pinch valve 62 by supplying air thereto. The delay timing cycle then begins again, as previously discussed. The material sampling device 1 of the present invention also includes a purge system. As previously noted, when rod 44 is in the fully retracted position, sensing valve 50 supplies an air signal through line 111 to actuator 77. Air is then supplied to pinch valve 62 cutting off the sample flow. Simultaneously, air is directed through a flow control valve 130 (which insures that a sufficient amount of air is supplied to pinch valve 62) and supply line 132 to check valve 64, thereby air flow is directed back through flex sample tube 52, hollow piston rod 44 and out collection head 8, thus purging the material sample conveying line. Check valve 64 is a one-way valve, and only allows air to flow during the purging cycle so that sample material can only flow in one direction during the sampling cycle, i.e. through pinch valve 62 and into sample storage area 54.

As can be seen in FIG. 2, collection head 8 includes a plurality of holes therethrough, which must reman perpendicular to the path of the conveyed bulk material to achieve optimum results. However, potential problems exist with conventional material samplers which may become angled across the conveying tube 2 in response to an uneven distribution of bulk material.

The following discussion will address the above mentioned problem in conjunction with a description of the operation of cylinder 42. FIG. 4 is a crossectional view of air cylinder 42 according to a first preferred embodiment of the present invention. Cylinder housing 43 and hollow piston rod 44 are shown with piston rod 44 having a threaded end 134 for attachment to connector 96 (FIG. 1). Channel 136 provides a path which allows for sample material to flow through cylinder 42. Threaded annular recess 138 provides means for connecting rod 44 to connector 56 and flex tube 52 (FIG. 1).

Cylinder end portion 47 includes elastomeric rod seal 140 and multiple elastomeric rod wipers 142. Seal 140 provides sealing engagement between rod 44 and housing 43, resulting in improved life and reduced maintenance of cylinder 42. Additionally, rod wipers 142 clean the outside surface of piston rod 44, such that any sample material adherred thereto which may contaminate or clog the inside of cylinder 42 is removed and does not enter chamber 48.

Moreover, FIG. 4 shows piston guides 144 which are cylindrical solid rods which are embedded, at one end, into cylinder housing 43. The other end of guides 144 are suspended within chamber 48 of cylinder 42. In the first preferred embodiment, two such guides, 144 are placed side by side in the same plane on which FIG. 4 lies. Piston 146 is of a cylindrical configuration and includes holes 148 therethrough. Piston guides 144 are inserted into holes 148 such that piston 146 is movable along guides 144 when air pressure is delivered by sensing valves 50 and 51 (FIG. 1. Piston seals 150 provide sealing engagement with the inside surface of chamber 48. Additionally elastomeric sealing material is placed between guides 144 and holes 148 such that air cannot pass through holes 148 when applied by sensing valve 50 and 51. Further, bumpers 152 are provided which cushion the impact between piston 146 and cylinder housing 43 as piston 146 moves linearly within chamber 48. Hollow piston rod 44 extends through the center axis of piston 146 and is attached by welding, brazing, or the like. Therefore, as piston 146 is driven within chamber 48, rod 44 also moves linearly within cylinder 42. Piston 146 moves in a direction away from sensing valve 50 or 51 which is supplying air pressure to cylinder 42. That is, when sensing valve 50 is providing air pressure, piston rod 44 is being extended and when valve 51 is supplying air pressure, piston rod 44 is being retracted. In this manner, collection head 8 (FIG. 2) can be inserted into and retracted from conveying portion 2 (FIG. 2) by cylinder 42, with hollow piston rod 44 being utilized to transport the sample material therethrough.

Therefore, the problem addressed above (i.e. turning of the collection head 8 within conveying tube 2) is solved because hollow piston rod 44 cannot turn on its linear axis (due to guides 144), and thus collection head 8 cannot turn within conveying tube 2. Piston guides 144 prevent rotation of hollow piston rod 44 about its linear axis even when collection head 8 confronts an uneven distribution of bulk material within conveying tube 2.

Figure 5:
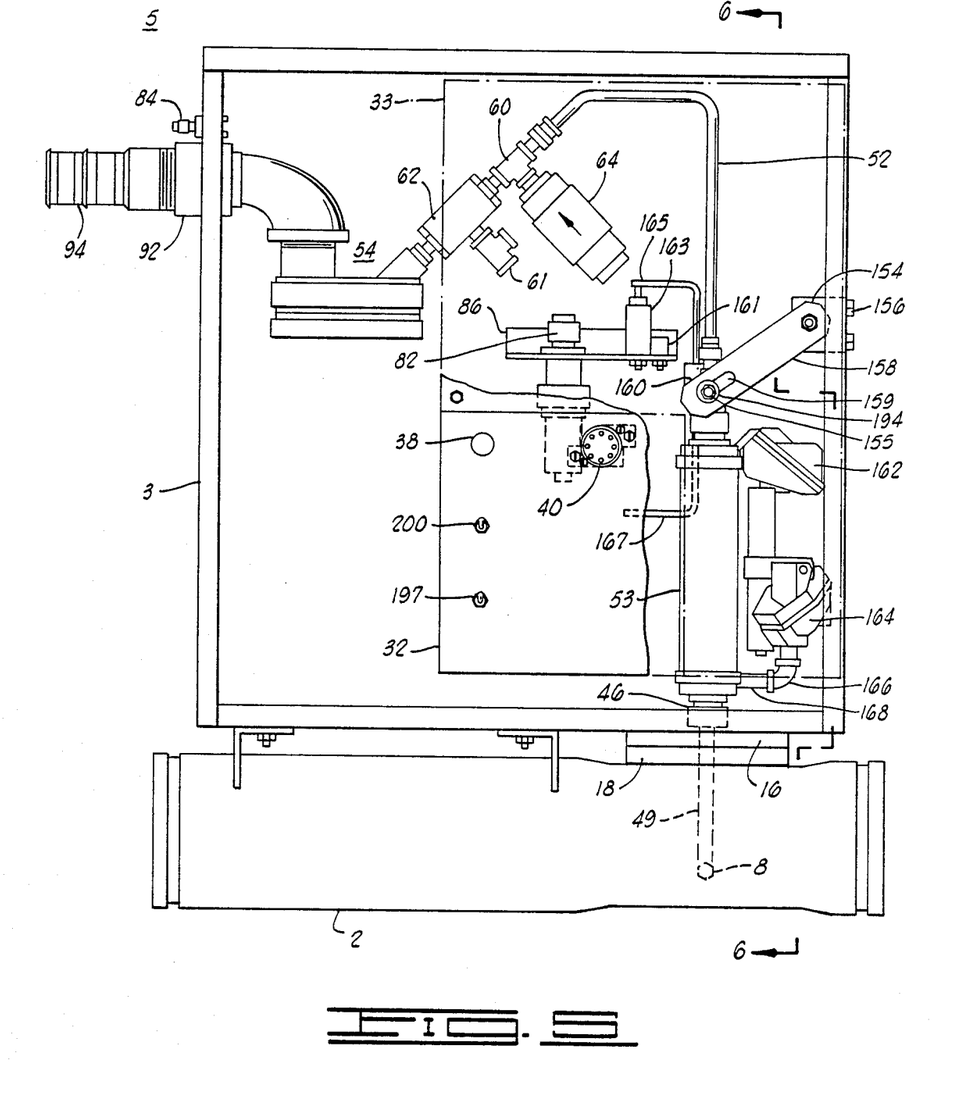
FIG. 5 is a front elevational view showing the components of a second preferred embodiment of the present invention.
Figure 6:
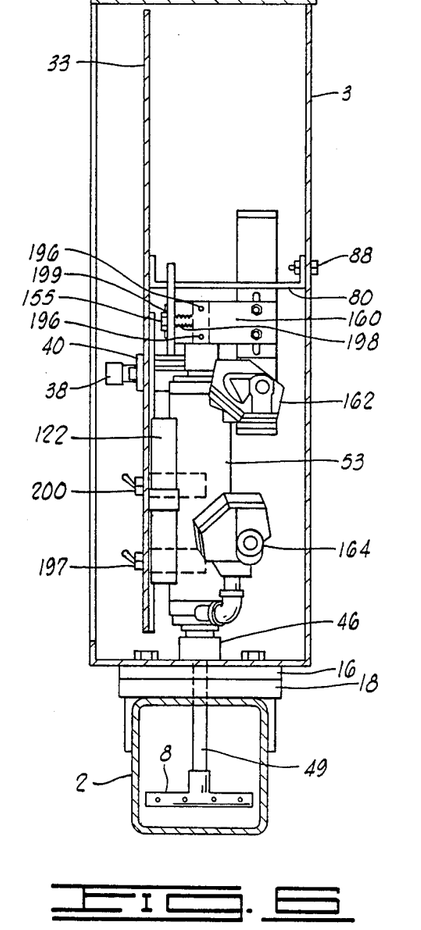
FIG. 6 is a side elevational view of the material sampler of the second preferred embodiment taken along line 6—6 of the FIG. 5.

Referring to FIGS. 5 and 6, a second preferred embodiment of the sampling device 1 of the present invention will hereinafter be described. Like reference numerals included herein pertain to the same components as previously described in conjunction with FIGS. 1, 2, 3 and 4.

FIG. 5 is an elevational view similar to FIG. 1 showing a sampling device 5 with elements which operate similarly including sample storage area 54, tee connector 60, pinch valve 62, check valve 64, flex sample tube 52, collection head 8 and conveying tube 2.

Hinge 154 is attached to enclosure 3 by threaded connectors 156, or the like. A support stabilizing arm 158 is included which includes a slot 159 therein. The support stabilizing arm 158 is attached at one end to hinge 154. A connector 160 surrounds the top portion of hollow piston rod 49 and is attached thereto by set screws 196 (FIG. 6), or the like. Connector 160 includes a threaded recessed area 198 such that a matching threaded bolt 155 is insertable therein. Threaded recess 198 is in communication with piston rod 49 within connector 160. Next, bolt 155 having a washer 199 thereon is inserted into slot 159 and threadedly engaged with recess 198. Bolt 155 is sized such that upon complete insertion into recess 198, contact with piston rod 49 is achieved thereby preventing any axial rotation thereof. Further, a limited clearance is provided between washer 199, stabilizing arm 158 and connector 160 such that up and down reciprocation of piston rod 49 is allowed. Thus, as hollow piston rod 49 extends and retracts, stabilizing arm 148 prevents collection head 8 from becoming angularly displaced across the crossection of conveying portion 2, due to a nonuniform distribution of bulk material flowing therethrough. Therefore, the second embodiment of the present invention solves the problem of collection head 8 turning about the linear axis of rod 49 by slot utilizing stabilizing arm 158 in conjunction with hinge 154, 159, connector 160 and bolt 155.

Quick release valves 162 and 164 are disposed at each end of cylinder 53 and input pneumatic power thereto for retracting and extending piston rod 49. Valves 162 and 164 operate such that when the air supply is stopped, they release the pressure which has built up within cylinder 53 at the cylinder 53, i.e. no pneumatic pressure flows back through modular valve 40. Valve 162 is directly connected to cylinder 53 whereas valves 164 uses a 90° ell 166 and nipple 168 to connect with cylinder 53. Three-way valve 161 and 4-way valve 163 are affixed to bracket 86, in the same manner as previously described with respect to valves 78 and 80.

FIG. 6 is a side elevational view taken along line 6—6 of FIG. 5. FIG. 6 shows collection head 8 extended into conveying portion 2 and perpendicular to the flow of bulk material therethrough. Additionally, quick release valves 162, 164, chamber 122, on/off valve 197, short-/long delay valve 200, long delay adjustment valve 38, modular valve 40 and panel 33 are illustrated in FIG. 6 and function with respect to the second preferred embodiment as described below.

Figure 7:
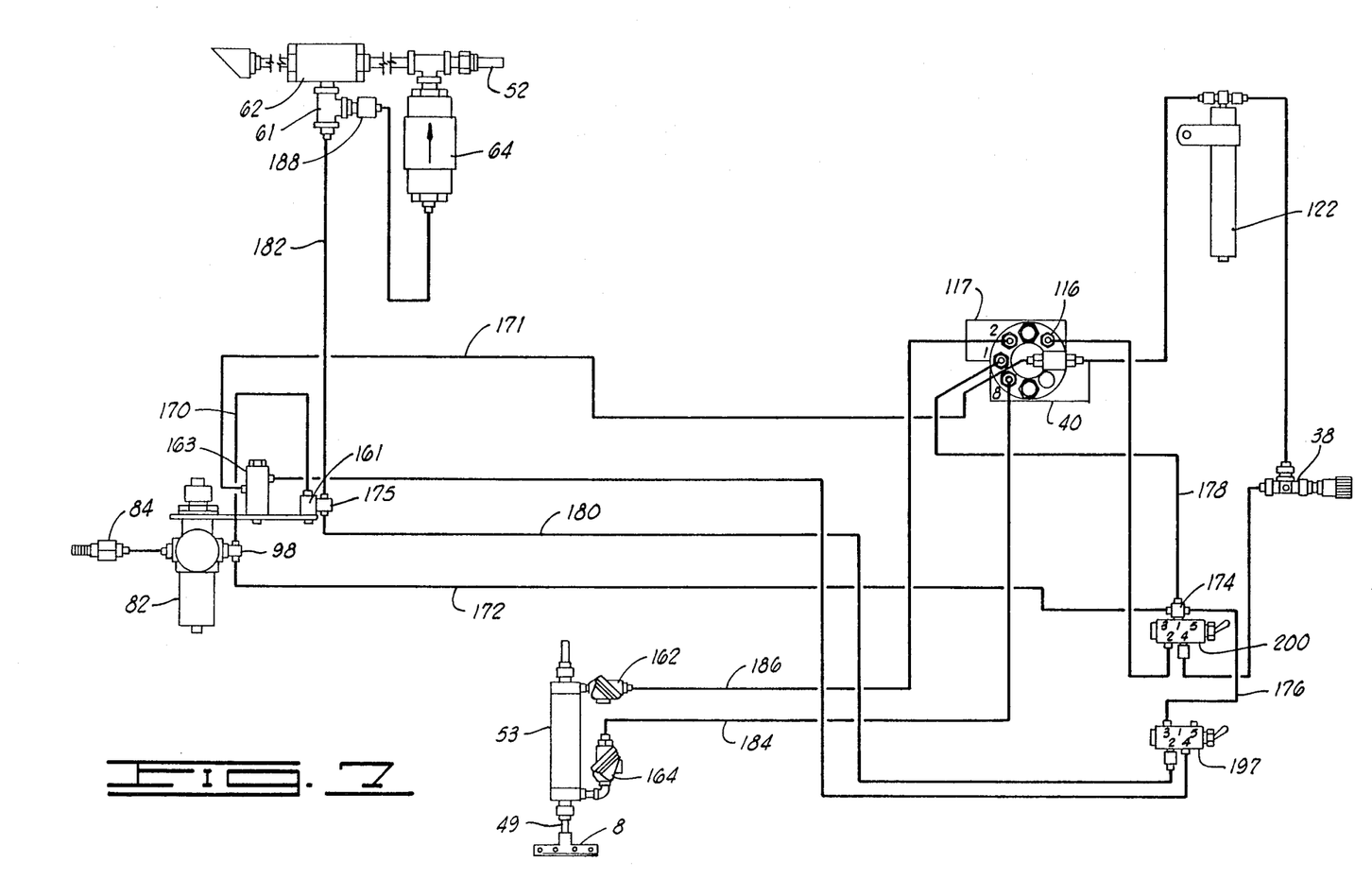
FIG. 7 is a schematic diagram of the pneumatic control circuit of the second preferred embodiment.

Next, the operation of sampling device 5 will now be described with reference to FIG. 7 wherein collection head 8 is in the retracted position and on/off valve 197 is in the "off" position. Plant air supply is input to fitting 84 and the pressure is then regulated and the air filtered by an air filter/regulator 82. Tee fitting 98 divides the air supply which is then input 3-way valve 161, via supply line 170, and to short/long delay valve 200, through supply line 172 and tee fitting 174. Pneumatic power is then supplied from tee fitting 174 to port 3 of on/off valve 197, via line 176, and port 1 of modular valve 40 through line 178.

In this phase of operation, air flows from port 3 to port 2 and on/off valve 197 and then on to tee fitting 175 through supply line 180. Air is then supplied to pinch valve 62 from tee fitting 175, through line 182 and tee connector 61. The air supplied maintains pinch valve 62 in a closed position such that no sample material can flow into sample storage area 54. Further, air is supplied to quick exhaust valve 164 from modular valve 40, via supply line 184, thus applying pressure to cylinder 53 which maintains piston rod 49 in a retracted position.

The operation of sample device 5 will now be described where the collection head is in a retracted position and the on/off valve 34 is in the "on" position.

Delay timing is initiated at the moment valve 197 is turned "on". The delay timing operation of the second preferred embodiment of the present invention operates in precisely the same manner as previously described with respect to the first preferred embodiment (FIG. 3). However, the sensing valves 50 and 51 have been replaced by quick exhaust valves 162 and 164, for the reasons set forth above. Additionally, a lower control arm 167 and upper control arm 165 are provided (FIG. 5), whereby lower control arm 167 actuates spring loaded 3-way valve 161 and resets 4-way valve 163, rather than pneumatic actuators 74, 76 and 77 (FIG. 3), which are utilized in the first preferred embodiment. Upper control arm 165 actuates 4-way valve 163 as piston rod 49 is extended downward. Both upper and lower control arms 165, 167 are adjustable such that proper contact with 3-way valve 161 and 4-way valve 163 can be easily achieved.

Air is supplied from port 2 of modular valve 40 to input valve 162 via supply line 186 which begins the extension of rod 49 from cylinder 53. Simultaneously, contact between lower control arm 167 and 3-way valve 161 is broken and the air pressure which is supplied to pinch valve 62 is relieved. Therefore, pinch valve 62 is opened and sample material may flow therethrough and into sample storage area 54.

Next, when piston rod 49 is fully extended, upper control arm 165 contacts 4-way valve 163, which has remained in the same state as when contacted by lower control arm 167 during a previous sampling operation, because valve 163 is not spring loaded. Upon contact by upper control arm 165, 4-way valve 163 shifts positions thereby sensing a pneumatic control signal to modular valve 40, via supply line 171, which in turn shifts positions thereby releasing air from the chamber 117 of modular valve 40 causing it also to shift. The shift of modular valve 40, directs air to quick exhaust valve 164 and initiates retraction of piston rod 49.

Pinch valve 62 remains open while piston rod 49 is being retracted and, similar to the previous embodiment, the flow of sample material into sample storage area 54 continues during this period. Once rod 49 is fully retracted, contact is reestablished between lower control arm 167 and valves 161 and 163 are actuated and reset. Therefore, air is once again supplied to close pinch valve 62, and to quick exhaust 164 which maintains rod 49 in the retracted position until a delay timing operation initiates extension of rod 49.

The second preferred embodiment also includes a purge function which operates similarly to the first preferred embodiment, as previously described. Briefly, air supplied to maintain pinch valve 62 in a closed position is exhausted, via tee connector 61 and choke 188 (which insures that enough pressure is maintained in pinch valve 62 to keep it in a closed position) to check valve 64 which then allows the air to flow back through flex sample tube 52, hollow piston rod 49 and collection head 8. Thus, any residual sample material is purged from the sample collecting device. Check valve 62 is a 1-way valve, and only allows air to flow during the purging cycle so that sample material can only flow in one direction during the sampling cycle, i.e. through pinch valve 62 and into sample storage area 54.

Figure 9:
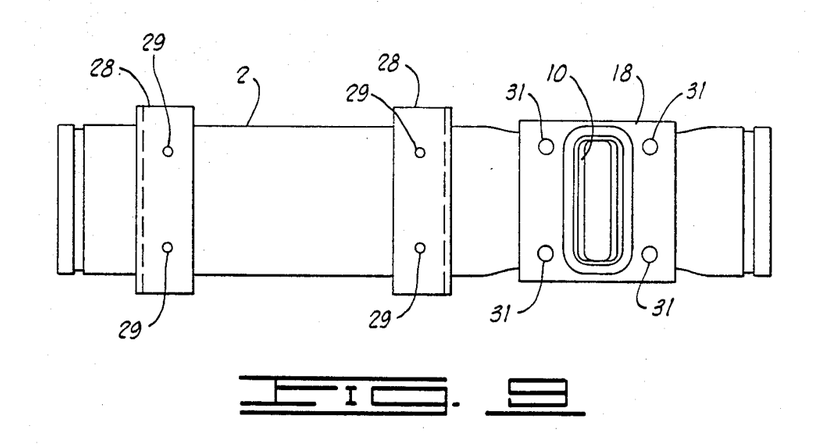
FIG. 9 is a top plan view, taken along line 9—9 of FIG. 1, of the cutout portions and connecting holes of the bulk material conveying tube which allow connection to the material sampling device.

FIG. 9 is a top plan view taken along line 9—9 FIG. 1 of conveying portion 2 with brackets 28 and mounting rim 18 shown thereon. Connectors 30 such as threaded connectors, or the like are inserted through holes 29 and attach enclosure 3 onto conveying portion 2 (FIG. 1). Mounting rim 18 and end plate 16 are rigidly affixed in layered relation to conveying portion 2 by connectors 24. Rectangular cutout portion 10 extends throughout rim 18 and conveying portion 2 and allows collection head 8 to be inserted into, and retracted from the bulk material flow path within conveying portion 2. Rim 18 defines retracted holding area 26 such that collection head 8 is stored out of the material flow path, when fully retracted.

The purge feature, as previously described, eliminates any need for a cover, or the like to prevent material from flowing into collection head 8 when in the retracted position. In both the first and second preferred embodiments air is supplied to purge the system during the entire time period that the collection head is retracted and the on/off valve is turned "on". This creates a positive pressure back through the sample material collection path which prevents any bulk material from flowing into the collection head 8 while in the retracted position.

Figure 8:
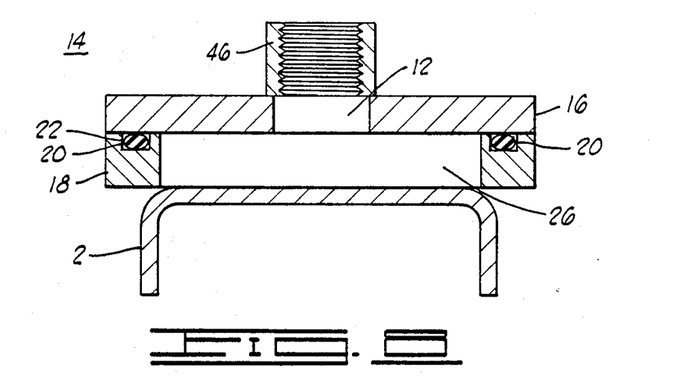
FIG. 8 is a crossectional view taken along line 8—8 of FIG. 1 of the connection between the material sampler and the bulk material conveying tube.

FIG. 8 is a crossectional view taken along line 8—8 of FIG. 1. Rim 18, plate 16 and conveying portion 2 are shown and function as previously described. Threaded end portion connector 190 (FIG. 4) is received by cylinder mounting 46. Retracted holding area 26 shows the area where collection head 8 will remain when in the retracted position.

Figure 10:
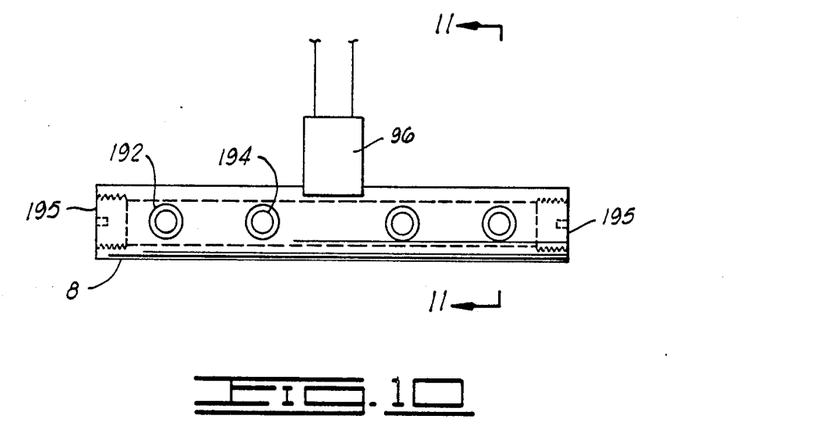
FIG. 10 is a front elevational view of the collection head of the material sampling device of the present invention.
Figure 11:
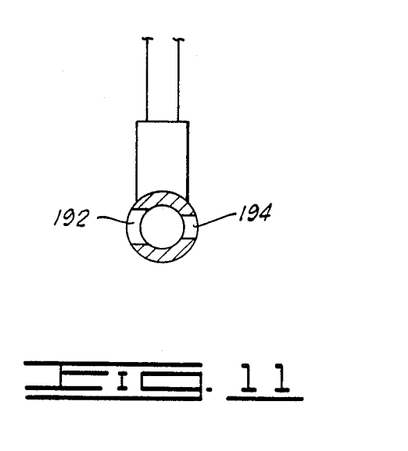
FIG. 11 is a side elevational view of the collection head as taken along line 11—11 of FIG. 10.

FIGS. 10 and 11 are a front view and side view of collection head 8. As can be seen, holes extend through collection head 8 which are perpendicular to the axis of collection head 8 and parallel to the flow path of bulk material through conveying portion 2. The front holes 192 are of a larger diameter than rear holes 194. This allows an adequate amount of sample material to flow into collection head 8 through front holes 192, while rear holes 194 prevent sample material from becoming clogged within collection head 8. Thus, the anti-clogging function of the first and second preferred embodiments of the present invention is an additional feature which improves upon conventional sampling devices and solves a problem experienced therein.

Additionally, should it be desired to access the inside of collection head 8 for cleaning or the like, plugs 195 which are threadedly engaged in the ends of collection head 8 can be removed.

Although certain preferred embodiments have been shown and described, it should be understood that many changes and modifications may be made therein without departing from the scope of the appended claims.

What is claimed is:

1. An apparatus for sampling bulk material flowing through a conduit, comprising:
   sampler means for receiving a sample of said bulk material;
   holding means for storing said material sample;
   drive cylinder means for inserting and retracting said sampler means into and out of a flow path of said bulk material,
   said drive cylinder means including a hollow piston rod directly connectable to said sampler means, the hollowed out portion of the piston rod thereby providing a flow passageway for said material sample; and
   control means for varying a frequency at which said sampler means is inserted into the flow path of said bulk material.

2. A sampling apparatus according to claim 1 wherein said apparatus further comprises transporting means for providing a flow passageway from said drive cylinder means to said holding means for said material sample.

3. An apparatus according to claim 1 wherein said drive cylinder means includes:
   a pneumatically operated cylinder having a piston of a smaller diameter and linear length than said cylinder;
   a first pneumatic input port; and
   a second pneumatic input port,
   wherein said first input port and said second input port emit a first and second position signal, respectively, based upon a position of said drive cylinder means; and wherein said piston is movable within said cylinder in a direction opposite the pneumatic input port to which pneumatic power is being applied.

4. An apparatus according to claim 3 wherein said hollow piston rod has a substantially cylindrical outer surface extending through a central axis of said piston, said hollow piston rod being of a greater length than said piston and said cylinder, and extending outwardly and along the axis of said cylinder.

5. An apparatus according to claim 4 wherein said hollow piston rod includes a cylindrical inner surface which defines the hollowed out portion of the piston rod as a hollow, tubular flow passageway therethrough.

6. An apparatus according to claim 4 wherein said cylinder includes at least one substantially cylindrical piston rod guide disposed therein and respectively extending through at least one respective associated hole defined within said piston, said at least one rod guide being sealingly and slidably engaged with said piston and providing rigid support thereto such that axial rotation of said hollow piston rod is prevented.

7. An apparatus according to claim 4 wherein said cylinder includes at least one wiper seal which cleans the outside surface of said hollow piston rod.

8. A sampling apparatus according to claim 3 wherein said control means includes:
regulator means for receiving pneumatic power from an outside source, and for regulating and filtering said pneumatic power;
timing means for receiving said pneumatic power from said regulator means, and for outputting a pneumatic drive signal to one of said first pneumatic input port and said second pneumatic input port, said pneumatic drive signal varying in accordance with predetermined manually input characteristics corresponding to the desired sampling frequency;
actuator means for receiving said first position signal from said first input port and said second position signal from said second input port, and for issuing a shift signal to said timing means; and
purge means for receiving a pneumatic purge signal from said actuator means, and for directing said signal through said flow passageway and said sampler means in a direction opposite to the direction in which said sample material flows.

9. An apparatus according to claim 8 wherein said timing means includes:
a manually operated needle valve which regulates a volume of pneumatic power which can pass therethrough;
a modular valve having a plurality of ports, a needle valve and a first pressure chamber contained therein;
a second pressure chamber having a specific volume which delays the transfer of pneumatic power to said first and second input ports until the pneumatic power within said modular valve is at a predetermined pressure level;
a first two-position valve having a first position which allows pneumatic power to be supplied to said timing means and a second position which does not allow air to be supplied to said timing means; and
a second two-position valve having a first position which allows pneumatic power to be supplied to said modular valve and a second position which allows pneumatic power to be supplied to said needle valve and said second pressure chamber.

10. An apparatus according to claim 8 wherein said purge means includes:
a check valve which allows pneumatic power to flow in a single direction; and
a pinch valve which restricts a flow of material therethrough upon receipt of a pneumatic power having a predetermined level.

11. An apparatus according to claim 1 wherein said sampler means includes a hollow cylindrical tube having a first plurality of holes defined therein along a first side of said tube and a second plurality of holes defined therein along said tube on a side opposite of said first side, wherein said plurality of holes are each of a diameter greater than each of said second plurality of holes.

12. An apparatus for sampling bulk material flowing through a conduit, comprising:
sampler means for receiving a sampling of said bulk material;
holding means for storing said material sample;
drive cylinder means for inserting and retracting said sampler means into and out of a flow path of said bulk material,
said drive cylinder means including a hollow piston rod directly connectable to said sampler means,
the hollowed out portion of the piston rod thereby providing a flow passageway for said material sample;
stabilizing means for maintaining said sampler means in a position perpendicularly across the flow path of said bulk material; and
control means for regulating the frequency at which said sampler means is inserted into the flow path of said bulk material.

13. A sampling apparatus according to claim 12 wherein said apparatus further comprises transporting means for providing a flow passageway from said drive cylinder means to said holding means for said material sample.

14. An apparatus according to claim 12 wherein said drive cylinder means includes:
a pneumatically operated cylinder having a piston of a smaller diameter and linear length than said cylinder,
a first pneumatic input port; and
a second pneumatic input port,
wherein said piston is movable within said cylinder in a direction opposite the pneumatic input port to which pneumatic power is being applied;
an upper control arm; and
a lower control arm,
wherein a position of said upper control arm and said lower control arm, with respect to the sampling apparatus, varies in accordance with a position of said sampler means.

15. An apparatus according to claim 14 wherein said hollow piston rod has a substantially cylindrical outer surface extending through a central axis of said piston, said hollow piston rod being of a greater length than said piston and said cylinder, said hollow piston rod having a first end and a second end and extending outwardly from and along the axis of said cylinder.

16. An apparatus according to claim 15 wherein said hollow piston rod includes a cylindrical inner surface which defines the hollowed out portion of the piston rod as a hollow, tubular flow passageway for said sample material to flow therethrough.

17. An apparatus according to claim 15 wherein said cylinder includes at least one wiper seal which cleans the outside surface of said hollow piston rod.

18. An apparatus according to claim 15 wherein said stabilizing means includes a stabilizing arm having a first end, pivotally disposed to said sampling apparatus, and a second end pivotally attached to said hollow piston rod, said stabilizing rod providing axial support to said hollow piston rod such that axial rotation thereof is prevented.

19. An apparatus according to claim 12 wherein said sampler means includes:
a hollow cylindrical tube having a first plurality of holes defined therein along a first side of said tube and a second plurality of holes defined therein along said tube on a side opposite of said first side, wherein said first plurality of holes are each of a diameter greater than each of said second plurality of holes.

20. A sampling apparatus according to claim 12 wherein said control means includes:
regulator means for receiving pneumatic power from an outside source, and for regulating and filtering said pneumatic power;
timing means for receiving said pneumatic power from said regulator means, and for outputting a pneumatic drive signal to one of said first pneumatic input port and said second pneumatic input port, said pneumatic drive signal varying in accordance with predetermined manually input characteristics corresponding to the desired sampling frequency;
switching means for contacting one of said upper control arm and said lower control arm, and for issuing a shift signal to said timing means; and
purge means for receiving a pneumatic purge signal from said actuator means, and for directing said signal through said flow passageway and said sampler means in a direction opposite to the direction in which said sample material flows.

21. An apparatus according to claim 20 wherein said timing means includes:
a manually operated needle valve which regulates a volume of pneumatic power which can pass therethrough;
a modular valve having a plurality of ports, a needle valve and a first pressure chamber contained therein;
a second pressure chamber having a specific volume which delays the transfer of pneumatic power to said first and second pneumatic input port until the pneumatic power within said modular valve is at a predetermined pressure level;
a first two-position valve having a first position which allows pneumatic power to be supplied to said timing means and a second position which does not allow air to be supplied to said timing means; and
a second two-position valve having a first position which allows pneumatic power to be supplied to said modular valve and a second position which allows pneumatic power to be supplied to said needle valve and said pressure chamber.

22. An apparatus according to claim 20 wherein said purge means includes:
a check valve which allows pneumatic power to flow in a single direction; and
a pinch valve which restricts a flow of material therethrough upon receipt of pneumatic power of a predetermined level.

* * * * *